(12) United States Patent
Walzman

(10) Patent No.: US 11,382,636 B2
(45) Date of Patent: *Jul. 12, 2022

(54) MESH CAP FOR AMELIORATING OUTPOUCHINGS

(71) Applicant: Daniel Ezra Walzman, Bergenfield, NJ (US)

(72) Inventor: Daniel Ezra Walzman, Bergenfield, NJ (US)

( * ) Notice: Subject to any disclaimer, the term of this patent is extended or adjusted under 35 U.S.C. 154(b) by 287 days.

This patent is subject to a terminal disclaimer.

(21) Appl. No.: 16/602,319

(22) Filed: Sep. 12, 2019

(65) Prior Publication Data

US 2020/0029973 A1   Jan. 30, 2020

Related U.S. Application Data

(63) Continuation-in-part of application No. 16/024,639, filed on Jun. 29, 2018, now Pat. No. 10,617,428,
(Continued)

(51) Int. Cl.
*A61B 17/12* (2006.01)
*A61M 25/00* (2006.01)
(Continued)

(52) U.S. Cl.
CPC .... *A61B 17/12172* (2013.01); *A61B 17/1215* (2013.01); *A61B 17/1219* (2013.01); *A61B 17/12031* (2013.01); *A61B 17/12036* (2013.01); *A61B 17/12113* (2013.01); *A61B 17/12145* (2013.01); *A61B 17/12177* (2013.01); *A61M 25/0021* (2013.01); *A61B 17/1214* (2013.01); *A61B 17/12186* (2013.01); *A61B 2017/00778* (2013.01); *A61B 2017/00818* (2013.01); *A61B 2017/00942* (2013.01); *A61B 2017/1205* (2013.01); *A61B 2017/12054* (2013.01);
(Continued)

(58) Field of Classification Search
CPC ........ A61B 17/12109; A61B 17/12031; A61B 17/1214; A61B 17/12113; A61B 17/12172; A61B 17/12; A61B 17/12177
USPC ........................................................ 606/200
See application file for complete search history.

(56) References Cited

U.S. PATENT DOCUMENTS

| | | |
|---|---|---|
| 3,874,388 A | 4/1975 | King et al. |
| 4,282,875 A | 8/1981 | Serbinenko |
| 4,346,712 A | 8/1982 | Handa et al. |
| 4,402,319 A | 9/1983 | Handa et al. |
| 4,619,246 A | 10/1986 | Molgaard-Nielsen et al. |

(Continued)

FOREIGN PATENT DOCUMENTS

| | | |
|---|---|---|
| WO | WO2011/057002 A2 | 5/2011 |
| WO | 2019/136218 A1 | 7/2019 |
| WO | PCT/US2020/050783 | 12/2020 |

*Primary Examiner* — George J Ulsh
(74) *Attorney, Agent, or Firm* — Ryan, Mason & Lewis, LLP

(57) ABSTRACT

An embolic device for ameliorating outpouchings, comprising a control element, a catheter element, a delivery microcatheter hypotube, a detachment element, a mesh disc, a distal opening and at least one attached extension arm, wherein said mesh disc further comprises a proximal face and a distal face, said proximal face being opposite of said distal face that are substantially flat. The mesh disc further comprises peripheral lips and a core having a diameter configured to be smaller than the target outpouching, the mesh disc being secured in place by at least one attached extension arm.

19 Claims, 6 Drawing Sheets

Related U.S. Application Data which is a continuation-in-part of application No. 15/732,519, filed on Nov. 20, 2017, now Pat. No. 10,543,015.

(60) Provisional application No. 62/600,134, filed on Feb. 13, 2017, provisional application No. 62/497,851, filed on Dec. 5, 2016.

(51) Int. Cl.
  *A61B 90/00* (2016.01)
  *A61M 25/10* (2013.01)
  *A61B 17/00* (2006.01)

(52) U.S. Cl.
  CPC .......... *A61B 2090/3933* (2016.02); *A61B 2090/3966* (2016.02); *A61M 25/10* (2013.01); *A61M 2025/0042* (2013.01); *A61M 2025/1047* (2013.01); *A61M 2210/12* (2013.01)

(56) References Cited

U.S. PATENT DOCUMENTS

| | | |
|---|---|---|
| 4,675,361 A | 6/1987 | Ward, Jr. |
| 5,165,421 A | 11/1992 | Fleischhacker et al. |
| 5,263,963 A | 11/1993 | Garrison et al. |
| 5,334,210 A | 8/1994 | Gianturco |
| 5,733,294 A | 3/1998 | Forber et al. |
| 5,907,893 A | 6/1999 | Zadno-Azizi et al. |
| 6,221,086 B1 | 4/2001 | Forber |
| 6,375,670 B1 | 4/2002 | Greenhalgh |
| 6,605,102 B1 | 8/2003 | Mazzocchi et al. |
| 7,575,582 B2 | 8/2009 | Gandhi et al. |
| 2001/0000797 A1 | 5/2001 | Mazzocchi |
| 2002/0042628 A1 | 4/2002 | Chin et al. |
| 2008/0033341 A1 | 2/2008 | Grad |
| 2010/0069948 A1 | 3/2010 | Veznedaroglu et al. |
| 2010/0198251 A1 | 8/2010 | Morsi |
| 2011/0144669 A1* | 6/2011 | Becking ............ A61B 17/12172 606/158 |
| 2018/0303489 A1 | 10/2018 | Walzman |

\* cited by examiner

MESH CAP FOR AMELIORATING OUTPOUCHINGS

CROSS-REFERENCE(S)

This is a continuation-in-part application claiming the benefit of priority to U.S. Non-Provisional application Ser. No. 16/024,639, filed Jun. 29, 2018 (29 Jun. 2018); Ser. No. 15/732,519 filed Nov. 20, 2017 (20 Nov. 2017); which claims priority to Prov. Appl. Ser. Nos. 62/600,134 filed Feb. 13, 2017 (13 Feb. 2017), and 62/497,851 filed Dec. 5, 2016 (5 Dec. 2016); the entire contents of which are incorporated by reference.

FIELD OF THE INVENTION

The described invention relates generally to endovascular devices generally, and more particularly to a specifically shaped support cap atop a mesh disc.

BACKGROUND OF THE INVENTION

The present invention is applicable to both gastrointestinal (GI) organs and brain aneurysms. The medical difficulty to which the present invention is applicable is outpouchings, which may refer to both diverticulum and aneurysms. More particularly, this disclosure relates to an endovascular device for filling of a vascular pathology, or other pathologic outpouchings. Outpouchings may include vascular aneurysms, be found in intracranial aneurysms; fusiform aneurysms, which consist of an outpouching of the arterial wall, without a stem; as well as saccular aneurysms, which consist of a neck, a stem, and a dome; as well as other vascular malformations. Depending upon which layers of the structure are involved, they are described as being either true or false. In medicine, the term usually implies the structure is not normally present. The medical or biological term diverticulum is usually used for gastrointestinal organs rather than vessels, referring to an outpouching of a hollow (or a fluid-filled) structure in the body.

Present actions for ameliorating cerebral outpouchings is performed by either an open surgical clipping of an aneurysm or via interventional endovascular procedures. Similar procedures for diverticular are also practiced for GI outpouchings. The most typical of such procedures involves the placement of one or more coils within the aneurysmal sac via a microcatheter, or similar procedures for GI outpouching difficulties. The primary limitation associated with vascular procedures is the fact so called "wide-necked" outpouchings (or aneurysms) are not generally amenable to this type of treatment due to the likelihood that the devices associated with said procedures will be displaced from the aneurysm sac. Another limitation associated with procedures which use a single thread coil device is that said device usually requires the surgeon to pack said coil within the aneurysm and thereby increasing the risk of damaging both the vessel and the aneurysm walls.

The prior art discloses the use of intracranial stents that have been developed for placement in the parent blood vessel to act as a buttress for holding the coil(s) in place within the aneurysmal sac in an effort to improve the retention of coils in outpouchings (or aneurysms) exhibiting such wide-necked anatomy. The fact that said stents must be placed in the brain is a limitation to this approach, due to the medical difficulties associated with damaging the blood vessels of the brain and increasing morbidity in both the short term as well as resulting in post-operative intracranial stenosis. Additionally, placement of such stents requires the use of oral dual antiplatelet therapy, to prevent in-stent thrombosis. The medications have potential bleeding complications. Furthermore, these medications are relatively contraindicated in the setting of a ruptured intracranial aneurysm, which often precludes the use of such stents in these settings.

While the prior art discloses the use of self-expanding coils such as US20100069948A1—Erol Veznedaroglu, said prior art discloses fail to provide a structure which decreases the permeability of blood across the neck of the outpouching, thus resulting in higher rates of coil compaction within said outpouching, and recurrence of the outpouching with its attendant risks. The present invention employs a mesh element, positioned predominantly across the neck of the aneurysm/out-pouching to surmount said limitation.

The prior art, including various Walzman inventions, disclose the use of various outpouch-filling devices and methods. These include hydrogel, hydrogel combined with coils, and so forth. Said prior art was primarily designed for vascular medical difficulties. The present invention is intended for both vascular and nonvascular outpouchings. The present invention specifically eliminates the use of hydrogel from all structures to better treat all types of outpouching. The use of hydrogel in some instances may exacerbate medical difficulties due to uneven swelling of the hydrogel, changes the delivery characteristics for the related medical devices adversely, and may be difficult to use in certain treatments. While the prior art discloses the use of a self-expanding mesh disc, positioned across the neck of an outpouching. For example, U.S. patent application Ser. No. 15/732,519 (Walzman '519), said prior-art disclosures fail to provide a structure which is immediately stabilized due to the lack of positioning elements suitable for gripping the aneurysmal wall. This lack of immediately stabilizing capability can result in the displacement of the device, thus necessitating the closing of said device, reposition of said device and redeployment of said device. Said closing, repositioning and redeploying takes time (when time is usually of the essence when dealing with aneurisms) and tends to damage vessel walls. Additionally, if said mesh disc apparatus is displaced after additional coils are deployed, repositioning of said apparatus may not be possible, and the malposition may result in permanent injury to the patient. The present invention employs mesh element as well as components that secure its position relative to an outpouching before detachment, and before placement of additional embolic materials when needed, to surmount said limitation. Thus, a self-expandable outpouching filling device the can both cover the neck of an outpouching and serve as a permanent embolic plug in the outpouching is desirable which is immediately stabilized. The present invention meets these and other needs. Thus, a self-expandable outpouching filling device the can both cover the neck of an outpouching and serve as a permanent embolic plug in the outpouching, with elements that promptly stabilize its position, with the mesh component in its desired position across the neck of the outpouching, but not projecting into the parent vessel, is desirable. The present invention meets these and other needs.

SUMMARY OF THE INVENTION

The present invention combines a disc disclosed in Walzman '519 application with self-expanding coil arms of memory material, such as wire to provide immediate stabilization. In some embodiments said coils are oriented to deploy into three dimensional structures.

The advantage of said coil arms is that they will provide a structure by which the mesh disc of the current invention can achieve more immediate and effective stable positioning, by the coil loops gripping the wall of the outpouching, with the mesh portion optimally positioned at the neck of the outpouching. Said coil loops may be spiral or connected in the form of a birdcage (or dome-shape) or similar structure. The prior art, however, teaches essentially spherical or ovoid configurations, and lacks the more effective dome-like shape and dense, somewhat flattened mesh at the bottom (neck of the outpouching) proximal to the distal end of the catheter.

GENERAL DESCRIPTION

Briefly, and in general terms, the present invention provides for a self-expandable outpouching-filling device for treatment of an outpouching, and a system and method for deploying the self-expandable outpouching filling device into the outpouching from a parent vessel for treatment of the outpouching to at least partially fill and stabilize the outpouching. In one aspect, the system provides a self-expandable outpouching filling device that can cover the neck of an outpouching, and can act as a permanent embolic plug in the outpouching. The self-expandable outpouching-filling device also provides a single, unified complex matrix that expands as it is deployed and achieves a generally half-spherical or semi-ovoid configuration, or other shapes such as pyramidal, kidney-shaped, bi-lobed, or other complex shapes, so that the self-expandable outpouching-filling device can be secured promptly in its desired position within the outpouching.

The optional configuration of the mesh disc of the device of the present invention can have a single layer, or be multi-layered. Other, optional embodiments of the mesh disc, in some iterations, include a central donut hole within it, to allow an easier access point for subsequent placement of additional embolic material, when desired. When present, said donut hole, in some iterations, can have its edges dimpled inward, to allow a cone-like region to facilitate reentry into the outpouching.

The mesh disc of the current invention is also detachable from the delivery wire, hypotube or microcatheter. In some iterations said microcatheter can extend through said disc near the distal end of said microcatheter, so that said microcatheter/hypotube can also subsequently serve directly as a route to deliver additional embolic materials into said outpouching. Said supplemental embolic materials may include coils, liquid embolic, hydrogel, combination devices, and other embolic materials known in the art. These may most often be deployed serially to fill the contours of an outpouching. One nonlimiting example of an outpouching is a vascular aneurysm.

The present invention provides for a self-expandable outpouching-filling device which is capable of immediately stabilization within moments of deployment. In some iterations, however, the coils/arms may spread out from there compressed state more slowly than said disc, to allow more precise positioning of said disc across the outpouching's neck, while avoiding the potential trauma of said coils/arms being dragged across the walls of said outpouching. The present invention includes a self-expandable outpouching filling device having a compressed undeployed configuration and an expanded three-dimensional deployed configuration, a delivery element (such as a wire or hypotube/microcatheter), and a severable deployment system including a junction capable of releasing said self-expandable outpouching filling device. The outpouching filling element of the present invention, in the preferred embodiment, is constructed of a metal such as platinum or platinum alloys, nitinol, and/or other biocompatible metals. The severable deployment element may be mechanically, electrolytically, or thermally, hydrostatically, chemically, or otherwise severed to separate the self-expandable outpouching filling device from the delivery element.

These and other aspects and advantages of the invention will become apparent from the following detailed description and the accompanying drawings, which illustrate by way of example the features of the invention.

BRIEF DESCRIPTION OF THE DRAWINGS

FIG. 3 also depicts an embodiment in which the delivery microcatheter 13 is a microcatheter capable of acting as a conduit for delivery of coils through it.

FIG. 3A also depicts an embodiment in which the delivery microcatheter 13 is a microcatheter capable of acting as a conduit for delivery of coils through it.

DETAILED DESCRIPTION OF THE INVENTION

Figure 1:
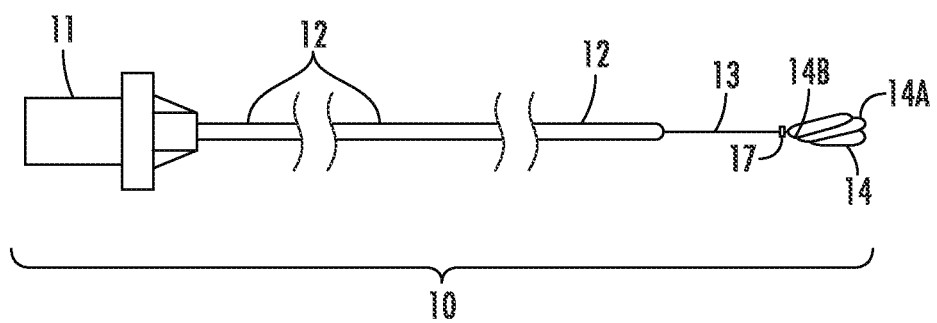
FIG. 1 depicts the present invention 10, including control element 11, catheter element 12 (in cutaway), delivery microcatheter element 13, detachment element 17, and a compressed, flexible mesh disc 14 with peripheral lips 14A, suitable for delivery through microcatheter element 13 and expanded upon release from constraint.

The present invention can be used with or without hydrogel 16. The preferred embodiment is without hydrogel. It should be noted that the current invention can be used with hydrogel, and such use has been disclosed in prior Walzman applications. When hydrogel is employed, hydrogel can optionally expand to a specific external stimulus only, rather than time of hydration. And can potentially shrink to an optional external stimulus. This on-demand expansion and shrinkage is helpful for repositioning medical tools near target areas inside veins and arteries. Said external stimuli include, but are not limited to, thermal, electrical, and/or chemical signals. It should also be noted that hydrogel 16 can optionally be radio-opaque, which facilitates remote locating and positioning of said hydrogel 16, this embodiment has been disclosed in prior applications, such as Walzman '519 and Ser. No. 16/024,673.

For the treatment of saccular outpouchings (or aneurysms): an endovascularly deployed mesh (metal mesh or other mesh) disc—which will optionally have two layers, like the inner disc of the Anplatz Left Atrial Appendage closure device currently in trials. The disc can have versions that are relatively flat, or some versions where the edges are folded up to accommodate differently shaped outpouchings (or aneurysms), including very wide neck outpouchings (or aneurysms). Such deviations from the generally flat plane of the mesh disc 14 of the current invention may have turned-up sides which conform to the walls of a target outpouching 100 which are proximal to the neck of said outpouching 100. Said upturned elements 14A (sometimes referred to as "lips") are optional and optimally used for very wide neck outpouchings (or aneurysms) that are less spherical in shape and more cylindrical in shape. With said more wide-neck outpouchings (or aneurysms) the anatomy does not lend itself to the deployment of a flat mesh disc 14 and at least one coil-arm 200, because wide neck outpouchings (or aneurysms) lack sufficient overhang regions at the neck to support the mesh disc.

Without such support said mesh disc 14 and at least one coil-arm 200 will be dislodged into the parent artery. The present invention teaches the use of multiple distinct lip configurations. The lip configurations differ in diameter, shape and orientation. In the preferred embodiment the central portion of the mesh disc (i.e. the portion closest to the delivery element, such as the wire or deliver microcatheter) will be oriented parallel to the neck of the target outpouching.

The diameter of the mesh disc ranges from 0.1 mm to 30 cm.

The shape of the mesh disc ranges from a circle to triangle. The shape is most typically round or oval.

In a typical spherical outpouching with a narrow neck, the entire mesh disc 14 and at least one coil-arm 200 include the lips and should be oriented parallel to the neck of the target outpouching. In this case, the lips overhang and rest on the base of the target outpouching, completely covering the neck of the target outpouching and extending over a portion of the adjacent base of the target outpouching and forming a base for at least one coil arm 200.

In a typical non-spherical outpouching with a wide neck, the entire outer perimeter of the mesh disc 14 should be oriented more perpendicular to the neck of the target outpouching than in the case of the typical spherical outpouching with a narrow neck, so as to gently grip the walls near the base of the target outpouching.

Referring now to FIG. 1, control element 11 is the user interface that has the optional capability of sending signals through catheter element 12, sometimes termed delivery catheter 12, and/or along delivery microcatheter 13, sometimes termed a hypotube 13. In some cases, the "microcatheter" 13 may be solid (such as when microcatheter 13 is a wire). Control element 11 is deployed outside the body containing the target outpouching. Control element 11 optionally deploys catheter 12 to a location proximal to the base of the neck of the target outpouching 100. Said control element 11 is optionally attached to catheter element 12 and/or optionally attached to delivery microcatheter 13 disposed therein. Said control element 11 is capable of sending signals via catheter element 12 and/or delivery microcatheter 13 to detachment element 17. In the preferred embodiment control element 11 is a separate detachment tool that is applied to the proximal side of delivery microcatheter 13 at the desired time, in order to detach the mesh disc 14 from said delivery microcatheter 13. Prior to deployment, additional contrast or other fluid injections can optionally be used to initiate deployment of optional balloon(s) 303 or 300 for the purpose of positioning catheter 12 so as to center delivery microcatheter 13 for optimal deployment of mesh disc 14. Detachment element 17 in turn may relay signals to mesh disc element 14. Said relay signals are capable of initiating the decompression of said mesh disc 14 and at least one coil arm 200 upon deployment. Alternatively, said compression may be automatic triggered by its release from constraints. Following deployment of said mesh disc 14 and at least one coil arm 200, control element 11 is optionally capable of sending signals which result in the deployment of coils 24, hydrogel 16, and/or lips 14A. In the preferred embodiment a separate control element 20 controls detachment of coils 24. Following deployment of the aforementioned elements, control element 11 is capable of signaling detachment element 17 to separate delivery microcatheter 13 from said mesh disc 14 and at least one coil arm 200. Control element 11 is then capable of retracting catheter 12 and delivery microcatheter 13. In the preferred embodiment, the control element 11 is commercially available.

Catheter 12 may have an outer diameter of 0.5 Fr-20 Fr. In the preferred embodiment catheter 12 has an outer diameter ranging from 3 Fr. to 5 Fr.

Note that the said mesh disc 14 and at least one coil arm 200 will be held in position upon deployment by coils 24 or hydrogel 16, each of which will substantially conform to the interior of target outpouching 100. Said coil arm may be a loop, or a straight extension. Said extensions may be of various widths and shapes. Some embodiments may have rounded atraumatic edges. Alternatively, mesh disc 14 must have up going "lips" and can be held in place by friction between said disc and the walls of the target outpouching, as well as the fact that disc 14 has a greater diameter than the diameter of the neck of the outpouching 100. Lastly, a larger disc 14 can be held in place both ways.

Mesh disc 14 and at least one coil arm 200 are compressible into a shape suitable for delivery through a catheter 12, and capable of expanding into a disc shape upon receipt of an electronic signal from control element 11, or upon release from its constraint. Said mesh 14 is capable of being coated with hydrogel 16, and holes in said mesh 14• are capable of storing said hydrogel 16 until deployment within said outpouching 100.

The amount of said hydrogel 16 may vary. The specific amount is not significant as long as sufficient hydrogel 16 is deliverable to the outpouching 100 to fill it. Other embodiments may use no hydrogel. In an alternate embodiment of the present invention, optional hydrogel coats mesh disc 14 and at least one attached arm extension 200 such that the hydrogel will expand into and filling the dome of said outpouching 100.

Mesh disc 14 and attached at least one arm extension 200 are releasably attached to delivery microcatheter 13 by detachment element 17.

Mesh disc 14 and at least one arm extension 200 are, in the preferred embodiment, radio-opaque or have radio-opaque marker or other positioning markers or incorporates other technology for remote visualization and location detection. The same characteristic is incorporated in detachment element 17.

Figure 2:
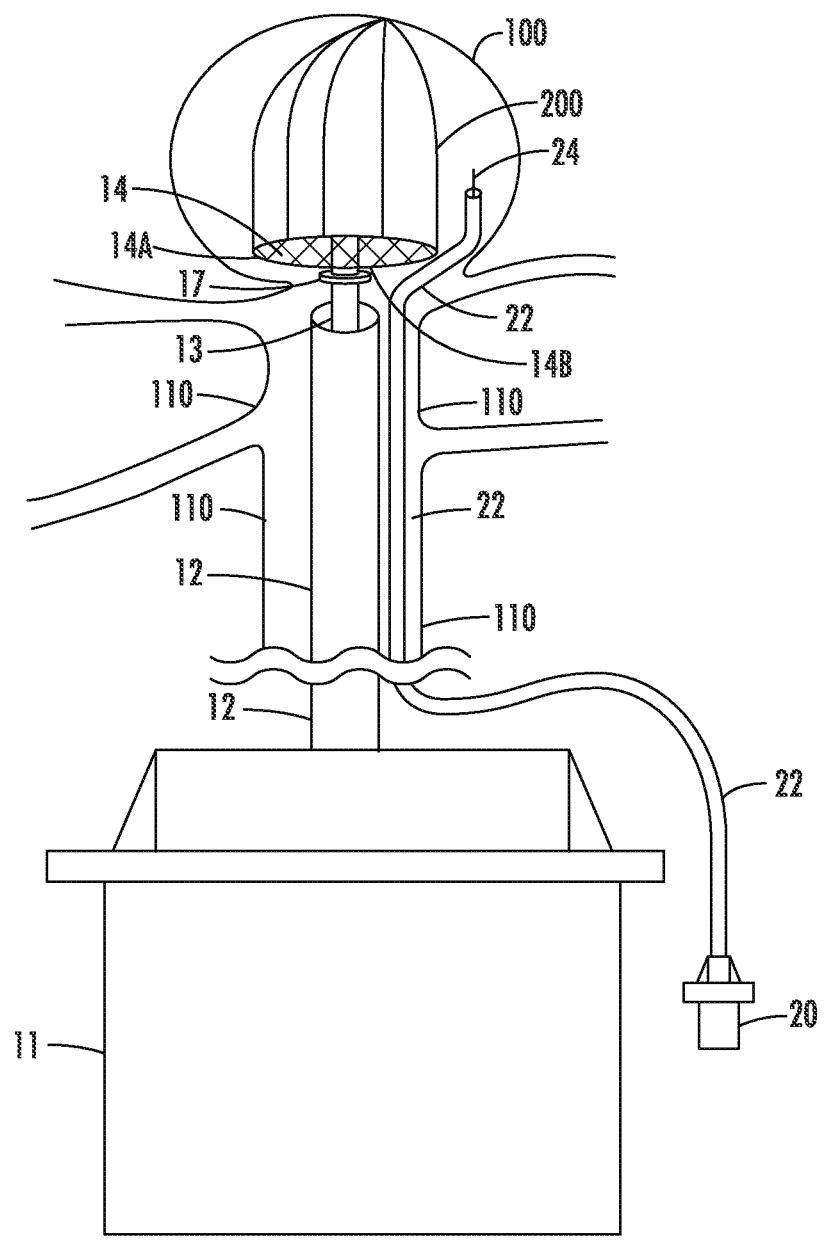
FIG. 2 depicts lips element 14A at periphery of flexible, substantially flat mesh disc 14 when uncompressed following delivery through and release from microcatheter 13 (said microcatheter 13 may be a solid wire, a microcatheter or a combination thereof) disposed within the neck of outpouching 100; along with a deployed prior art device composed of control element 20, catheter 22, wire coil 24, and at least one coil-arm (or attached arm extensions) 200 introduced into an outpouching 100 such as a saccular aneurysm. Said coil arm extensions 200 provide supplemental support to be secured with an outpouching. Said securement, unlike the prior art, provides a mesh disc with multiple attachment points within an outpouching. More particularly, mesh disc 14 comprises a core 14B having a diameter configured to be smaller than target outpouching 100. Mesh disc 14B is secured in place by at least one attached extension arm 200.

Referring now to FIG. 2, the mesh disc 14 and at least one coil arm 200 are deployed through delivery catheter 12 passing through vessel 110 to the base of the neck of target saccular outpouching 100. Control device 11 may optionally signal delivery microcatheter 13 to extend beyond the distal end of catheter 12 in a length sufficient to enter target outpouching 100 to allow deployment of mesh disc 14 and at least one coil arm 200. Once the progress of delivery microcatheter 13 ceases, control element 11 signals mesh disc 14 and at least one coil arm 200 to deploy. Mesh disc 14 and at least one coil arm 200 enter the target outpouching in a compacted form, said signal from control element 11 directs said mesh disc 14 and at least one coil arm 200 to open as a blossom to allow the perimeter of said mesh disc 14 and at least one coil arm 200 to overlap the base of the neck of the outpouching 100. In the preferred embodiment the delivery catheter 12 is manually held in place while the delivery microcatheter 13 is manually advanced forward in a length sufficient to enter target outpouching 100 to allow deployment of mesh disc 14 and at least one coil arm 200. Mesh disc 14 and at least one coil arm 200 enter the target outpouching in a compacted form and as it is released from its constraint said mesh disc 14 and at least one coil arm 200 open as a blossom to allow the perimeter of said di mesh disc 14 and at least one coil arm 200 to overlap the base of the neck of the outpouching 100. The disc is then gently pulled back manually into position, which is determined preferentially by fluoroscopic and/or angiographic images.

The present invention employs a control element 11. Said control element's function is to detach mesh disc 14 and at least one coil arm 200 at a specific time. Control element 11 may be combined with control elements of various devices which may be used with the present invention. Control element 11 may incorporate mechanical, chemical, hydrostatic, electrical and/or thermal means for implementing the function of detaching mesh disc 14 and at least one coil arm 200.

Continuing to refer to FIG. 2, such deployment can accompany the deployment of existing devices which disrupt the flow across the neck of an outpouching 100, such as prior art coil 24 in the saccular aneurysm as illustrated in FIG. 2 deployed by a second control element 20 through second catheter 22. It should be noted that mesh disc element 14 of the present invention is capable of resulting in a second "jailed" microcatheter.

Figure 3A:
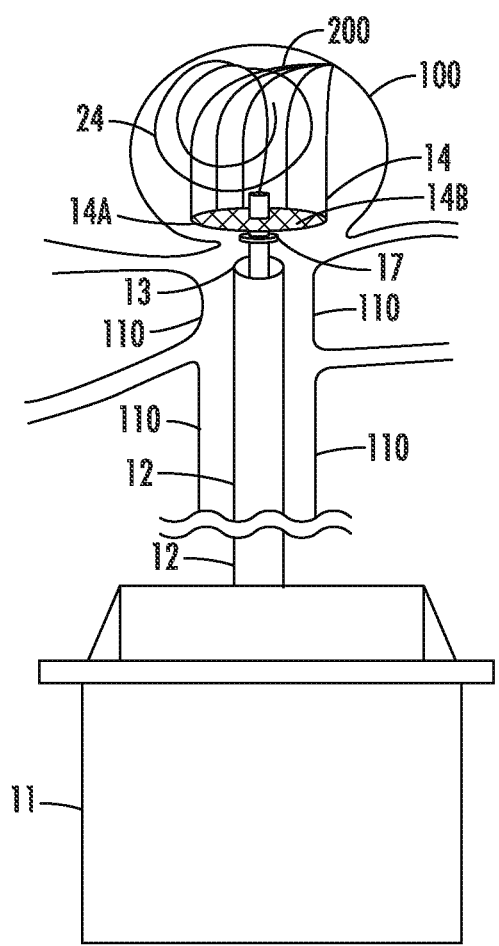
FIG. 3A depicts the present invention 10 deployed through vessel 110 with mesh disc 14 deployed at base of neck of a targeted, non-spherical outpouching 100, integrating wire coil element 24 of the prior art.
Figure 3B:
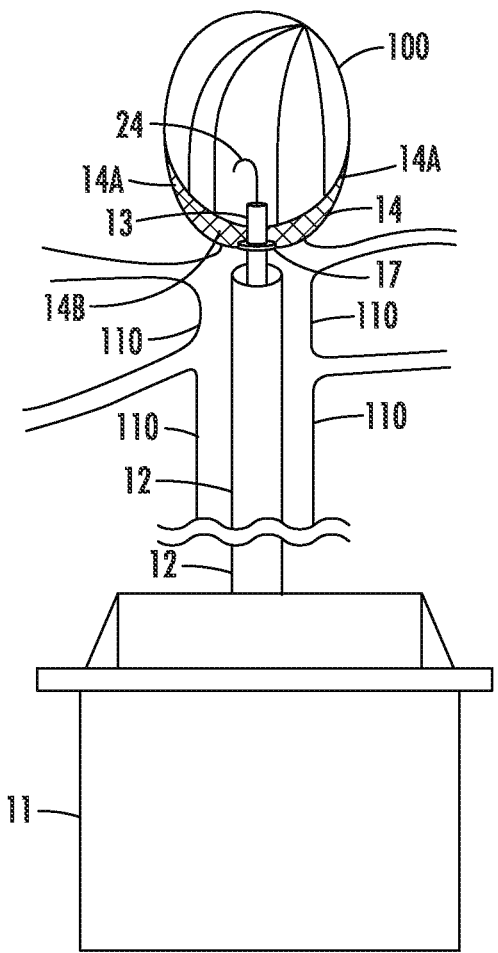
FIG. 3 depicts the present invention 10 deployed through vessel 110 with mesh disc 14 deployed at base of neck of a target spherical outpouching 100, integrating wire coil element 24 of the prior art capped by a birdcage (or dome) cover formed of coil-arms 200.

Referring now to FIG. 3, the present invention may incorporate elements of the prior art, such as the deployment of coils 24 through microcatheter 13.

Referring now to FIG. 3A, the present invention teaches the use of up turned lips to secure said mesh disc.

Figure 4:
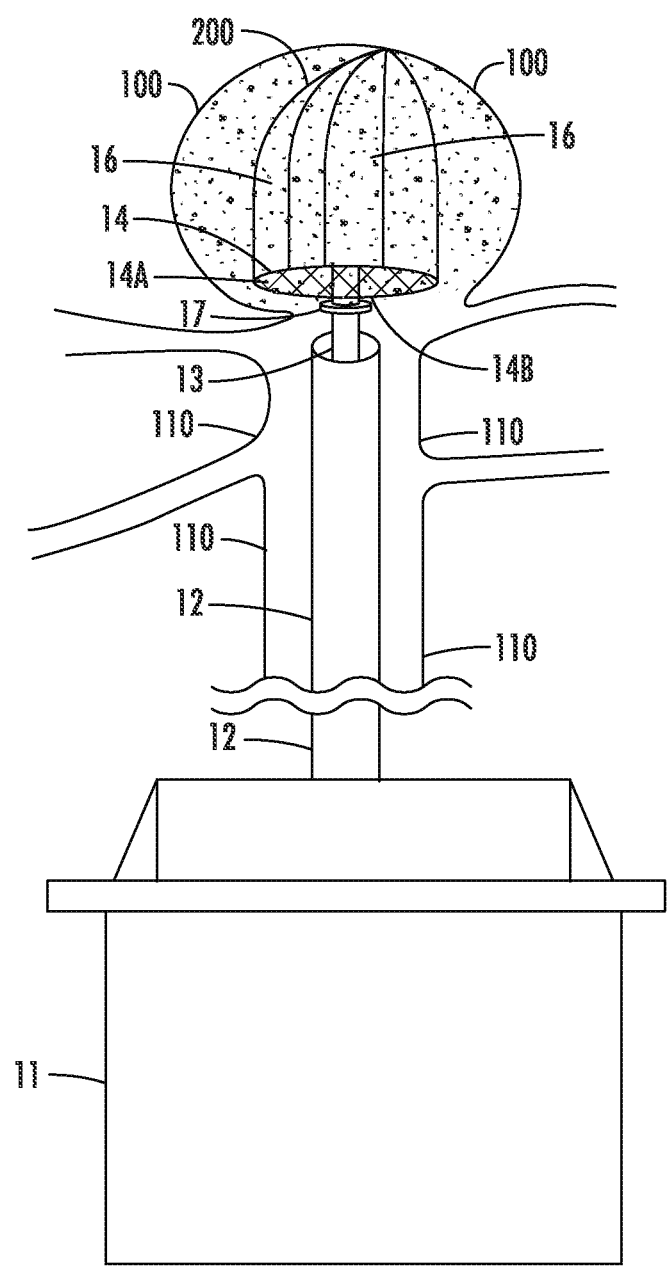
FIG. 4 illustrates an alternate embodiment of the present invention, deploying coil-arms 200 in conjunction with activated (i.e., swollen) hydrogel 16 within target outpouching 100.

Referring now to FIG. 4, an alternate embodiment of the present invention deploys mesh disc 14 and at least one coil arm 200 in conjunction with semitransparent, activated/swollen hydrogel 16. Hydrogel 16 can be deployed on the surface of mesh disc 14 and at least one coil arm 200, via a hollow in delivery microcatheter 13, via a second device (not shown), or via a second wire (not shown) deployed through catheter element 12. Alternatively, the hydrogel 16 may be deployed via the mesh disc 14 and at least one coil arm 200. Alternatively, hydrogel embedded coils may be used with the present invention.

Figure 5:
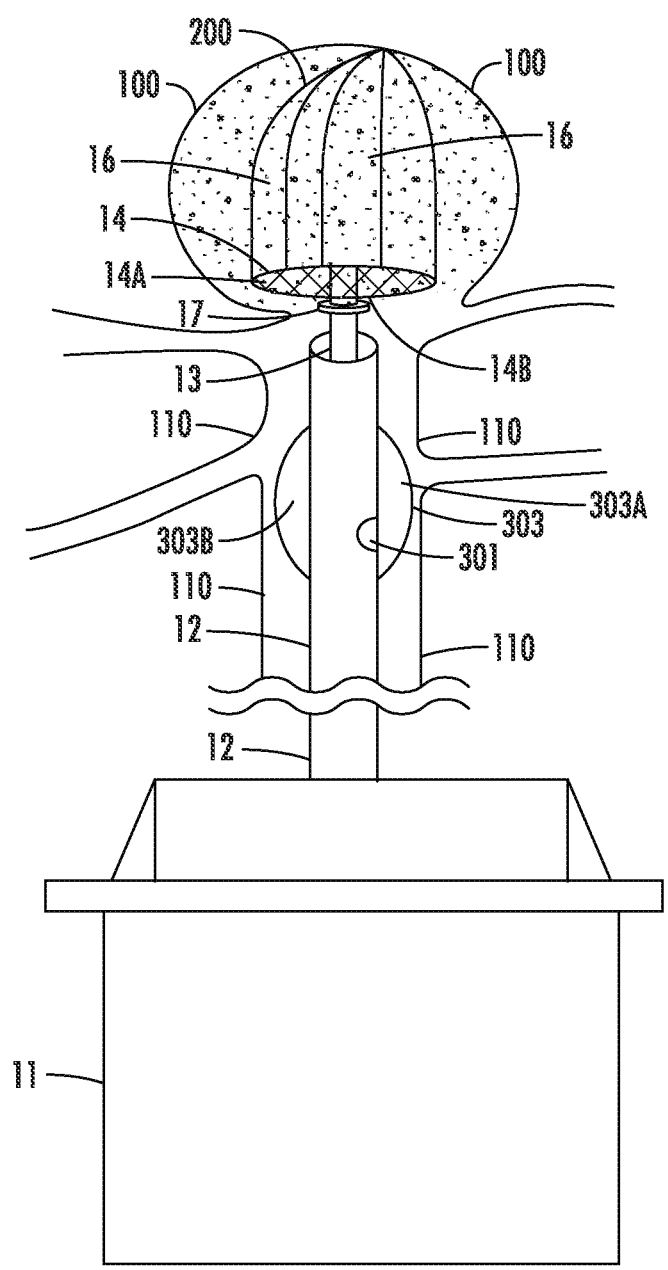
FIG. 5 depicts an alternate embodiment of the hydrogel 16 impregnated device including the coil-arms 200 of FIG. 4, further including optional centering balloon 303 to position catheter element 22 more precisely in relation to the center of the neck of target outpouching 100.

Referring now to FIG. 5, an alternate embodiment of FIG. 4 further includes a centering balloon 303 within vessel 110. Centering balloon 303 allows catheter element 12 to be positioned more precisely and stably in relation to the center of the neck of target outpouching 100. Referring more particularly to centering balloon 303, said balloon is described in detail in Walzman application Ser. No. 15/482,436 (entitled Vessel access catheter), incorporated herewith by reference.

It should be noted that Walzman application Ser. No. 15/482,436 (entitled Vessel access catheter), incorporated herewith by reference describes both single balloons and balloon arrays. The present invention's centering balloon 303 may be either a single balloon or a balloon array. Said single balloon or balloon arrays are designed to help center the tip of catheter element 12 to a location proximal to the center of the target outpouching. Said positioning may be achieved by the inflation of at least one balloon in order to deflect catheter element 12 in a desired direction.

Figure 6:
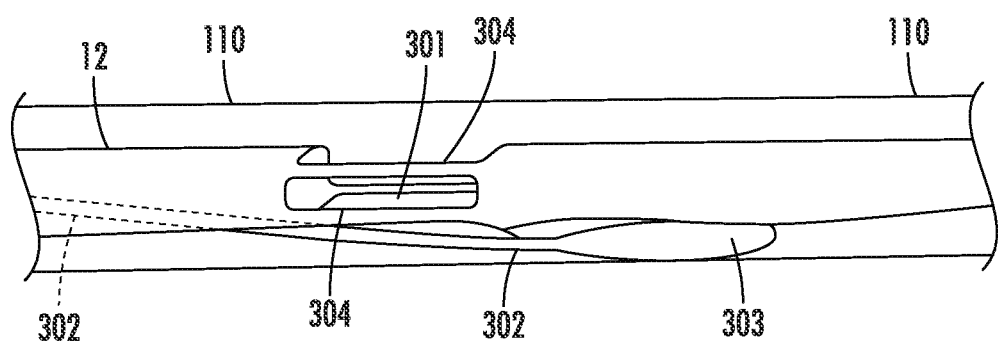
FIG. 6 illustrates a detailed deployment of an optional disc balloon.

An additional embodiment of the current invention incorporates the Walzman disc balloon 300, as illustrated by FIG. 6, into catheter element 12. Said incorporation is an alternate embodiment which is designed to help center the tip of catheter element 12 to a location proximal to the center of the target outpouching. It may also act as vertical positioning element by abutting the base of the mesh disc during positioning in the target outpouching.

Both balloon embodiments separately or in combination are also designed to arrest flow within the vessel proximate to the target outpouching when fully inflated. Said inflation will result in control of unwanted bleeding in case of target outpouching rupture.

Thus, the present invention can have several different embodiments, including:

First, a disc alone—an appropriately sized disc—can be deployed through a microcatheter in a saccular aneurysm, after a second microcatheter is placed in the microcatheter. The disc is gently pulled back to the neck of the outpouching, bridging said neck, and with a lip beyond the open portion of the neck to stabilize the disc. The disc is not detached at first, but remains tethered to its delivery system (a wire or catheter). Were it to be deployed early it would likely migrate into the outpouching and be ineffective and sometimes dangerous. Through the second microcatheter, which is now "jailed" in the outpouching, appropriately sized coils are sequentially placed and deployed into the outpouching per current routine protocols/techniques, until the outpouching is adequately filled with coils. The second microcatheter is removed. At this point the disc is detached from its delivery wire/catheter, which is removed.

Second, a disc mounted on a hypotube or microcatheter 13 which is introduced into outpouching through a slightly larger catheter, wherein the hypotube or microcatheter goes through the disc to just beyond it. An appropriately sized disc can be deployed through a microcatheter in a saccular aneurysm. The disc is gently pulled back to the neck of the outpouching, bridging said neck, and with a lip beyond the open portion of the neck to stabilize the disc. The disc is not detached at first but remains tethered to its delivery catheter/hypotube. Were it to be detached early, it would likely migrate into the outpouching and be ineffective and sometimes dangerous. Through said delivery catheter/microcatheter, appropriately sized coils are sequentially placed and deployed into the outpouching per current routine protocols/ techniques, until the outpouching is adequately filled with coils. At this point the disc is detached from its catheter/hypotube. The catheter/hypotube is then removed.

Third, a hydrogel enhanced disc alone. The disc is an endovascularly deployed mesh composed of a shape-memory material such as nickel-titanium alloy or other memory-shape material capable of super-elastic properties, such that the compressed mesh disc will revert to its flat-mesh disc shape upon release or activation by an electronic or light impulse. It will optionally have two layers like to inner disc of the Anplatz Left Atrial Appendage closure device currently in trials—the disc can have versions that are relatively flat, or some versions where the edges are folded up to accommodate different shape outpouchings (or aneurysms), including very wide neck outpouching. In this version, however, the outside surface of the disc facing into the outpouching is lined with a non-biodegradable hydrogel, that when exposed to blood upon deployment, will swell over a prescribed time (10 minutes in the preferred embodiment of the present invention), to conform to the size and shape of the outpouching, and fill and occlude said outpouching. The other layer of the disc that is closer to the parent artery can optionally have thin layers of hydrogel as well—but this layer would have hydrogel designed only to swell to occlude that layer of disc alone, so no hydrogel from the other layer can potentially expand through the mesh into the parent vessel. An appropriately sized disc can be deployed through a microcatheter in a saccular aneurysm. The disc is gently pulled back to the neck of the aneurysm, bridging said neck, and with a lip beyond the open portion of the neck to stabilize the disc. The disc is not detached at first but remains tethered to its delivery system (a wire or catheter). Were it to be detached early it would likely migrate into the outpouching and be ineffective and sometimes dangerous. The disc is held in place at the neck of the outpouching, while the hydrogels swell. Once the prescribed time is elapsed and follow up angiography confirms occlusion of the outpouching, the disc is detached from its delivery wire/catheter, and the delivery wire/catheter and the microcatheter through which it was deployed are removed. Optionally in appropriate circumstances, hydrogel may be used in filling the outpouching, which occludes that outpouching and also stabilizes the disc in place (in example 1 and 2 above the coils achieve these 2 goals). It should be noted that prior Walzman disclosures have claimed such embodiments.

Fourth, all features of the first through third above and optionally; plus the disc can have a smaller metal core disc 14B dimensioned smaller than the diameter of the outpouching and has hydrogel designed to expand out in a disc like shape from the edges, to make a larger disc that can then be gently dragged into position. It can then be pinned in place by coils or optional hydrogel embedded in the top of the disc, that also then expands into the dome of the outpouching, either via a layer on the top of the metal disc designed to expand after the side hydrogel, or via a separately implanted hydrogel bead or the like.

A smaller disc can also be used in combination with other embolic fillers, wherein said disc is secured by said at least one arm extension, and said disc serves to reduce the effective width of the neck of said outpouching.

The mesh disc 14 and at least one coil-arm 200 may also optionally be delivered through a disc balloon microcatheter (previously described by Walzman Ser. No. 15/732,170) or a similar configuration (disc balloon), an intermediate catheter, or another balloon catheter. These can serve as methods for delivering the present invention. Said method(s) may also be used to deliver any mesh intrasaccular device including other devices taught by the prior art, such as the Web and the Luna.

The advantage of a delivery through a disc balloon microcatheter is twofold. First, the balloon may sometimes be helpful positioning the mesh disc 14 and at least one coil-arm 200, and second, that in the event the outpouching ruptures during treatment, the balloon can be inflated to arrest flow and control active bleeding until more coils can be placed.

Said disc and said coil loops vary in size and in the time necessary to fully deploy. More particularly, the diameter of said discs vary from 0.1 mm-500 mm. The diameter of said coil loops vary from 0.1 mm-1000 mm. The length of said coil loops can be 0.1 mm-3142 mm long Coil loops for coil invention are typically sized in diameter of the target outpouching.

With respect to the time necessary to fully deploy said disc and said coil vary from nearly instantaneous [approximately one second or less] to one hour. While in some embodiments both said disc and said coil expand at the same rate, in other embodiments said disc and said coil expand at independent rates. In some embodiments said coil expands faster than said disc and in other embodiments said disc expands faster than said coil.

In the preferred embodiment said coils complete their expansion approximately forty-five (45) seconds after said disc completes its expansion. This time off set allows the present invention to be positioned into optimal position across neck (the opening) of the target outpouching without dragging metal under outward tension along said target outpouching or vessel walls thus eliminating or ameliorating medical difficulties such as breaching said outpouching or said vessel walls. Said breaches can result in injury or death to a patient.

The present invention has four structural optional elements. Said optional element are central donut holes in the disc element of the present invention; single or multiple mesh layer(s) in the disc element of the present invention; hydrogel coating on all or parts of the disc element of the present invention; and hydrogel coating of all or parts of the coil arm element(s) of the present invention.

More particularly, the donut hole structure in the disc element of the present invention is optional. One embodiment of the present invention has a central donut hole structure. Another embodiment of the present invention does not have a central donut hole structure.

More specially, the single layered mesh configuration of the present configuration is optional. One embodiment of the present invention has a single mesh layer in the disc element of the present invention. Another embodiment of the present invention the present invention has multiple mesh layers in the disc element of the present invention.

More expressly, the application of a hydrogel coating of the disc element of the present invention is optional. One embodiment of the present invention discloses a hydrogel coating on the surfaces of the disc element of the present invention. In another embodiment of the present invention said hydrogel coating is not applied to the surfaces of the disc element of the present invention. In other embodiments, a hydrogel coating is employed on some but not all surfaces of the mesh disc. In some optional embodiments the hydrogel is chemically optimized to expand significantly, and may also be positioned so that it expands, into the pathological outpouching, to further aid in the thrombosis/closure of said aneurysm/outpouching.

More especially, the application of a hydrogel coating of the coil arm element(s) of the present invention is optional. One embodiment of the present invention discloses a hydrogel coating on the surfaces of the coil arm element(s) of the present invention. In another embodiment of the present invention said hydrogel coating is not applied to some of the surfaces of the coil arm element(s) of the present invention. In yet another embodiment of the present invention said hydrogel coating is not applied to any of the surfaces of the coil arm element(s) of the present invention.

Although the invention has been described in detail in the foregoing embodiments for the purpose of illustration, it is to be understood that such detail is solely for that purpose, and that variations can be made therein by those skilled in the art without departing from the spirit and scope of the invention, except as it may be described by the following claims.

What is claimed is:

1. An embolic device for ameliorating an outpouching, comprising a control element, a catheter element, a delivery microcatheter hypotube, a detachment element, a mesh disc, a distal opening and at least one attached extension arm, wherein the mesh disc further comprises a proximal face and a distal face, the proximal face being opposite of the distal face; and the proximal face and the distal face are substantially flat; wherein the mesh disc further comprises peripheral lips; wherein the mesh disc comprises a core having a diameter configured to be smaller than a dimension of an outpouching, wherein the mesh disc is secured in place by the at least one attached extension arm.

2. The device according to claim 1, wherein the mesh disc with the at least one attached extension arm comprises a matrix adapted to form shapes of suitable geometry for adapting to contours of the outpouching.

3. The device according to claim 1, wherein the delivery microcatheter hypotube further comprises a channel capable of delivering at least one coil therethrough.

4. The device according to claim 3, further comprising at least one coil to be delivered through the channel of the delivery microcatheter hypotube.

5. The device according to claim 4, further comprising a matrix of coils deliverable through the delivery microcatheter hypotube, the matrix adapted to form shapes of suitable geometry to fill the outpouching.

6. The device according to claim 1, wherein the mesh disc is configured to be impregnated with adhered hydrogel in a sufficient amount to wedge the mesh disc into the outpouching.

7. The device according to claim 6, wherein the adhered hydrogel is radio-opaque.

8. An embolic device for ameliorating an outpouching, comprising a control element, a catheter element, a wire, a detachment element, a mesh disc, at least one arm extension adhered to the mesh disc, and a distal opening, wherein the mesh disc further comprises a proximal face and a distal face, the proximal face being opposite of the distal face; and the proximal face and the distal face being substantially flat;
wherein the mesh disc further comprises peripheral lips, and a disc core having a diameter configured to be smaller than a dimension of an outpouching, and wherein the mesh disc is secured in place by the at least one arm extension.

9. The device according to claim 8, wherein the mesh disc includes the at least one arm extension comprises a matrix adapted to form shapes of suitable geometry for conforming to contours of the outpouching.

10. The device according to claim 9, wherein the matrix is configured to substantially fill the outpouching.

11. The device according claim 8, wherein the mesh disc and the at least one arm extension are configured to be impregnated with adhered hydrogel in a sufficient amount to wedge the mesh disc into the outpouching.

12. The device according to claim 8, wherein the mesh disc is configured to be positioned at a neck of the outpouching.

13. The device according to claim 8, wherein the mesh disc further comprises at least one additional layer.

14. The device according to claim 13, wherein the at least one additional layer further includes the adhered hydrogel adapted to alter flow through only the one additional layer.

15. The device according to claim 12, wherein the mesh disc with the at least one arm extension is adapted to grip walls of the outpouching, and configured to stabilize the mesh disc in position at the neck of the outpouching.

16. The device according to claim 8, further comprising a delivery microcatheter hypotube, the microcatheter hypotube comprising a channel capable of delivering at least one coil therethrough.

17. The device according to claim 16, further comprising at least one additional coil that is delivered through the microcatheter hypotube.

18. The device according to claim 17, wherein the at least one additional coil comprise a matrix adapted to form shapes of suitable geometry to fill the outpouching.

19. The device according to claim 8, wherein the mesh disc with the at least one arm extension is dimensioned to grip walls of the outpouching, and configured to stabilize the mesh disc in position at a neck of the outpouching.

* * * * *